United States Patent [19]

Ishikawa et al.

[11] Patent Number: 5,626,824
[45] Date of Patent: May 6, 1997

[54] AUTOCLAVE

[75] Inventors: Yoichi Ishikawa; Shuji Yokoo; Akira Mizoguchi, all of Tokyo, Japan

[73] Assignee: Able Corporation, Tokyo, Japan

[21] Appl. No.: 565,258

[22] Filed: Nov. 30, 1995

Related U.S. Application Data

[63] Continuation of Ser. No. 188,040, Jan. 28, 1994, abandoned.

[30] Foreign Application Priority Data

| Jan. 29, 1993 | [JP] | Japan | 5-049835 |
| Mar. 29, 1993 | [JP] | Japan | 5-108698 |

[51] Int. Cl.$^6$ ............................................. A61L 9/00
[52] U.S. Cl. ................ 422/307; 366/208; 366/210; 366/211; 422/295; 422/297; 422/298; 422/299; 422/300; 422/309
[58] Field of Search ................................. 422/307, 309, 422/295, 297, 298, 299, 300; 366/110–112, 114, 116, 314, 276, 208, 210, 211, 213, 216

[56] References Cited

U.S. PATENT DOCUMENTS

| 1,491,031 | 4/1924 | Chapman . | |
| 1,709,175 | 4/1929 | Huygen . | |
| 2,499,203 | 2/1950 | Warren . | |
| 4,045,185 | 8/1977 | Azemar et al. | 23/290 |
| 4,097,235 | 6/1978 | Stock . | |
| 4,170,421 | 10/1979 | Balding et al. . | |
| 4,702,610 | 10/1987 | Reynolds, Jr. | 366/111 X |
| 5,119,994 | 6/1992 | Placzek | 422/295 X |
| 5,217,688 | 6/1993 | Von Lersner | 422/309 X |

FOREIGN PATENT DOCUMENTS

| 0424561 | 10/1989 | European Pat. Off. . |
| 2055289 | 3/1981 | United Kingdom . |

OTHER PUBLICATIONS

Patent Abstracts of Japan, vol. 6, No. 63, 22 Apr. 1982 & JP-A-57 005 678.

*Primary Examiner*—Robert J. Warden
*Assistant Examiner*—Krisanne M. Thornton
*Attorney, Agent, or Firm*—Flynn, Thiel, Boutell & Tanis, P.C.

[57] ABSTRACT

An autoclave (1) is provided with an internal table (1) upon which articles to be sterilised can be placed. The autoclave is provided with a mechanism (2, 3, 5) for shaking or vibrating the table, and thereby shaking or vibrating the liquid undergoing sterilization, resulting in a more even temperature distribution within the liquid, thereby reducing the length of time for sterilization and reducing the occurrence of flash evaporation of the culture medium. The shaking or vibration may, for example, be induced by a shaft (2) which passes sealingly through a wall of the autoclave or may be induced by a number of magnets (41) located on a ring (38) around the autoclave which magnetically attract associated magnets (35) on the table within the autoclave.

2 Claims, 4 Drawing Sheets

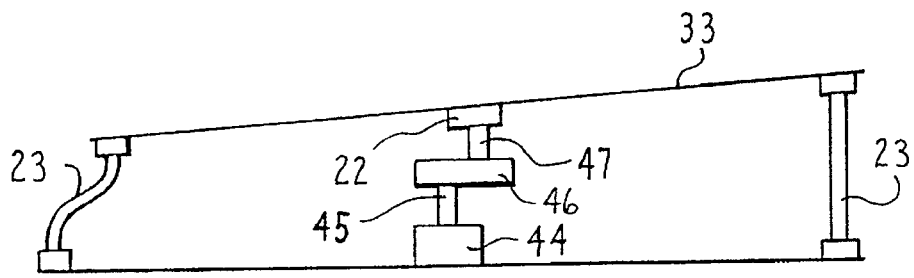
FIG. 8
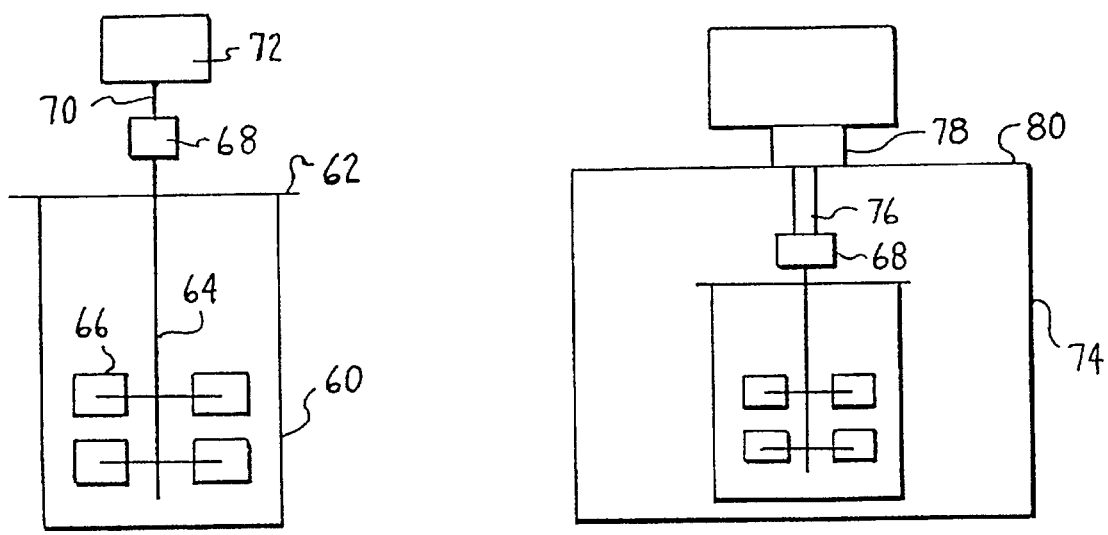
FIG. 9
PRIOR ART
FIG. 10
PRIOR ART

1

AUTOCLAVE

This application is a continuation of U.S. Ser. No. 08/188 040, filed Jan. 28, 1994 now abandoned.

DESCRIPTION

The present invention relates to the sterilization of a liquid in an autoclave, and in particular, but not exclusively, to the sterilization of culture media for fermentation.

In order to sterilize a culture medium held in a fermenter or a flask, the fermenter or flask is placed in an autoclave where it is subjected to a high temperature and/or pressure, for example by supplying pressurised steam to the interior of the autoclave.

In known autoclaves or fermenters heat transfer is generally achieved mainly by convection, resulting in a wide range of temperature distribution within the liquid. It is known for culture media in large autoclaves to be agitated by pivoting the tank in a vertical plane (i.e. about a horizontal axis) in order to narrow the range of temperature distribution, but this method cannot be applied to sterilize a liquid held in a container within the autoclave, since the liquid would overflow from the container.

In conventional autoclaves in which no agitation device is provided, the range of temperature distribution in the tank of the autoclave as well as the temperature distribution of liquid within the container are wide, as mentioned previously. It is thus often necessary to set the temperature within the tank of the autoclave to a higher level than might be expected, to carry out the sterilization completely, in order to ensure that all of the culture medium reaches at least a set sterilization temperature in advance.

It is thus desirable for liquids undergoing sterilization in the autoclave to be agitated during sterilization. Agitation narrows the temperature distribution within the liquid and enables sterilization to be completed earlier. A shorter sterilization period can be important, since many culture media are susceptible to thermal denaturing and a shorter sterilization period also reduces the energy required for sterilization. Narrowing the range of temperature distribution within the liquid also permits a set sterilization temperature to be efficiently achieved.

Also, after sterilization, the autoclave is allocated to cool. During cooling of the autoclave the temperature of the liquid within the autoclave decreases without maintaining an equilibrium of vapour pressure. If the vapour pressure becomes seriously out of equilibrium, flash evaporation of the liquid can occur..Agitation of the liquid allows the liquid and the vapour pressure to be more in equilibrium, thus reducing the likelihood of flash evaporation.

The reduction in sterilization temperature can also reduce the amount of energy required for sterilization.

Agitation of the liquid is also desirable when the liquid contains solid matter, in order to carry out the sterilization correctly and efficiently.

A known autoclave capable of agitating a culture medium located within it during sterilization is provided with a rotary shaft which passes sealingly through the wall of the tank of the autoclave. The end of the shaft within the autoclave is provided with agitation blades and the shaft is rotatably driven from outside the autoclave. The agitation blades are located within the liquid and during sterilization the liquid can be agitated by rotating the shaft.

Similarly, a known, small-sized fermenter has a rotary agitation shaft passing sealingly through a head plate of the fermenter vessel which can be driven by a motor on the exterior of the vessel. The culture medium is held in the vessel itself, but the agitating means may only be operated during fermentation. If it is desired to sterilize the culture medium within the fermenter vessel by means of an autoclave, it is necessary to disconnect the motor before placing the fermenter vessel in the autoclave. Thus, the means for agitating the culture medium in the fermenter vessel during fermentation cannot be used to agitate the culture medium during sterilization.

An autoclave which is capable of stirring a culture medium undergoing sterilization has a rotary shaft which passes sealingly through the wall of the tank of the autoclave and which is driven by a motor.

FIG. 9 shows a fermenter in the form of a fermenting vessel 60 and a head plate 62. A shaft 64 passes sealingly through the head plate. The lower end of the shaft is provided with agitation blades 66 and the upper end of the shaft is secured to a connector 68 which in turn is releasably secured to, and rotatable by means of, the output shaft 70 of a motor 72 in order to agitate a culture medium during fermentation.

If it is desired to place the fermenter in an autoclave 74 and continue agitation of the medium, as shown in FIG. 10, it is necessary for a different output shaft 76 of the motor 72 to pass through a seal 78 located on a head plate 80 of the autoclave and to be releasably secured to the connector 68. Operation of the motor thus enables the culture medium to be agitated during operation of the autoclave.

Although this arrangement permits agitation during sterilization, it is necessary for the rotary agitation shaft extending into the autoclave or fermenter to be specially formed in order to be releasably and drivably connected to the shaft extending into the vessel. In particular, this device does not permit agitation of a medium held in a vessel which has not been specifically adapted, such as a conventional flask placed within the autoclave for sterilization.

It is an object of the present invention to provide an autoclave which narrows the range of temperature distribution in a liquid to be sterilized, whereby the sterilizing time and/or sterilizing temperature can be reduced, in order to save energy and to reduce the likelihood of thermal denaturing of the sterilized liquid.

In accordance with the present invention, there is provided an autoclave comprising a sterilizing tank for holding an item to be sterilized, which is characterised by agitating means for shaking or vibrating at least a portion of the tank during sterilization.

The present invention permits agitation of a liquid undergoing sterilization within an autoclave without the requirement for the releasable connection of an agitation shaft with a rotary shaft as in the prior art. In addition, the present invention is capable of agitating a culture medium even in a conventional container within which the medium is contained does not have an agitating device, and in particular the present invention permits a considerable reduction in the range of temperature distribution within the culture medium undergoing sterilization.

The tank may comprise a table upon which the items undergoing sterilization are supported, and which is shaken or vibrated in order to agitate the items. The table may be rotatably or eccentrically mounted and may in addition be mounted to induce a seesaw motion of the table.

In one embodiment, the shaking or vibration is induced by a shaft secured to the table and passed sealingly through a wall of the tank.

In another embodiment, agitation is achieved by magnets located on a rotatably mounted ring around the periphery of the tank which attract associated magnets.

The term "shaking" generally means an action at a frequency no greater than 500 Hz, and includes the case where the motion of a portion of the tank (e.g. a table) is discontinuous, for example where rotation of a portion of the tank is interrupted and/or reversed. "Vibration" relates to an action at a frequency higher than 500 Hz. The possible agitation actions include vertical and lateral actions, eccentric rotations, seesaw motion, pendulum motion and a combination thereof. In one embodiment an agitation system known as a "belly dancer" is used, which employs a combination of an eccentric rotation and a seesaw motion, and operates at no greater than 200 revolutions per minute, this system being particularly advantageous for a large autoclave.

In the present invention there are various types of shaking or vibrating methods which can be used selectively according to the particular purpose. In the present invention, both the gas in the autoclave and a liquid to be sterilized are agitated so that the range of temperature distribution of both the gas and liquid are reduced. Thus, the measurement of the temperature of the autoclave can be conducted accurately with the knowledge that the temperature of the liquid to be sterilized will rise speedily. This reduces the time required to sterilize the culture medium and is particularly advantageous when a large quantity of liquid is to be sterilized, particularly because it can reduce the thermal denaturing of the medium.

If the sterilised container is moved when the sterilization of a culture medium has just been completed with the container still hot, flash evaporation of the culture medium can occur in some cases as a result of the temperature distribution within the medium. However, this phenomenon is greatly reduced with the present invention as a result of the much more even temperature distribution.

BRIEF DESCRIPTION OF THE DRAWINGS

By way of example only, specific embodiments of the present invention will now be described, with reference to the accompanying drawings in which:

FIG. 8 is a detailed side elevation cross-section of a portion of a seventh embodiment of the present invention;

FIG. 9 is a schematic cross-sectional side elevation of a known fermenter having means for agitating a culture medium during fermentation; and FIG. 10 is a schematic cross-sectional side elevation of the fermenter of FIG. 9 being used in conjunction with a known autoclave.

Figure 1:
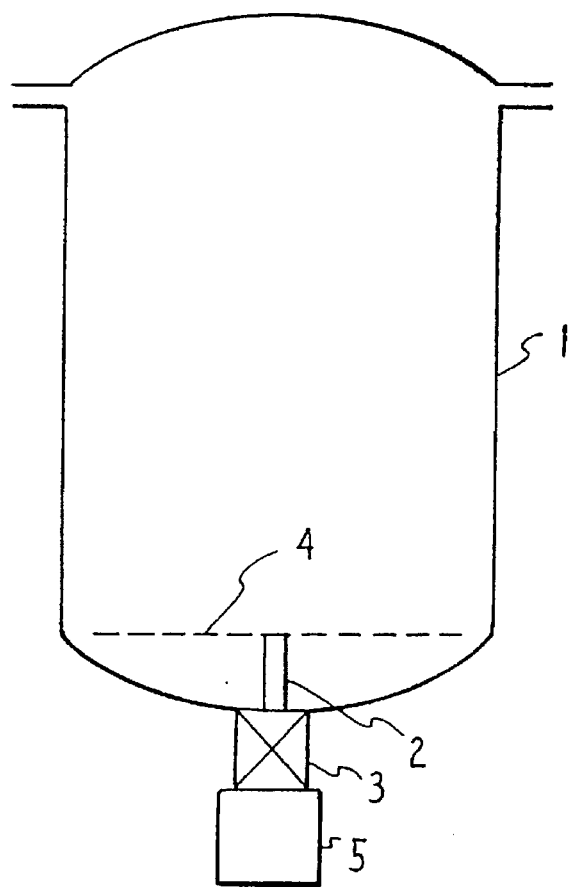
FIGS. 1 to 5 are schematic cross-sectional side elevations of first to fifth embodiments respectively.

The first embodiment, illustrated in FIG. 1, comprises a conventional autoclave tank 1 through the base of which a rotary shaft 2 passes sealingly by means of a mechanical seal or oil seal 3. A shaking or vibrating table 4 (which is preferably perforated) is fixedly secured to the upper end of the rotary shaft 2 within the autoclave tank and the shaft 2 and table 4 secured thereto are rotatable by means of a motor 5 located externally of the autoclave tank. The motor 5 can be rotated in either direction and the direction of rotation can quickly and repeatedly be changed by means of the motor.

In use, liquid to be sterilised in a container is placed on the shaking or vibrating table 4 and the autoclave is heated in a conventional manner (e.g. by means of a heater or gas to generate vapour in order to sterilize the liquid. The motor is actuated, whereby the rotation of the motor is transmitted directly to the rotary shaft 2, to the table 4 and to the liquid located in the container positioned on the table 4. The rotation of the table is preferably frequently stopped and the direction of rotation reversed so that the liquid within the container is agitated, thereby causing the liquid to circulate to a greater extent and reducing the temperature differences within the liquid.

For example, the table may be rotated in a first direction at a speed of from 10 to 100 r.p.m. for a period of from 1 to 20 seconds. The table may then be stopped for a period of from 1 to 20 seconds. The table is then rotated in the opposite direction at a speed of from 10 to 100 r.p.m. for a period of from 1 to 20 seconds. The table is then stopped again for 1 to 20 seconds, whereupon the above cycle is repeated. The table is thereby shaken, resulting in agitation of liquid in a container located on the table.

Figure 2:
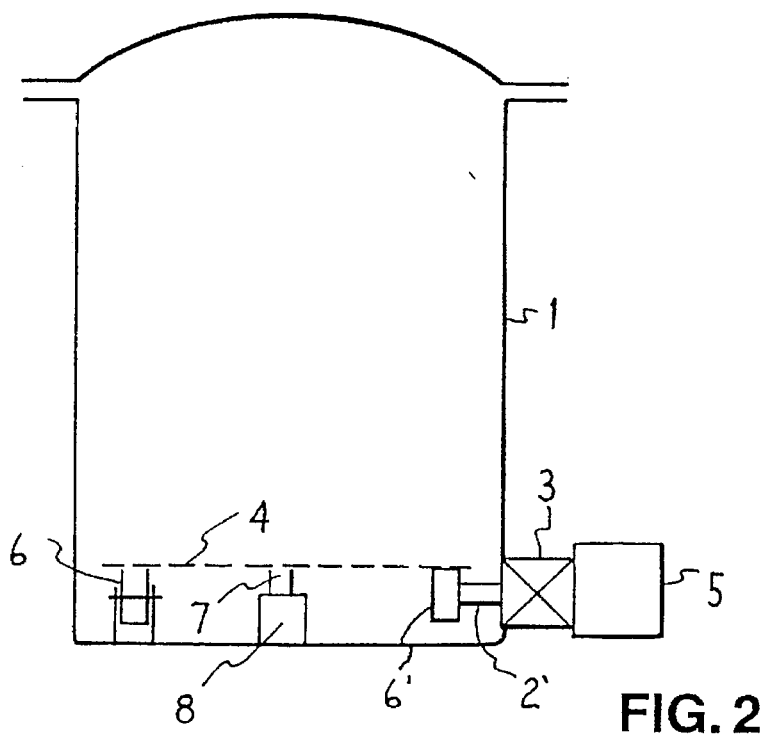

A second embodiment of the present invention is illustrated in FIG. 2. Many of the features of the later embodiments are very similar to those of the first embodiment, and have been given the same reference numerals as in the first embodiment. A shaking or vibrating table 4 is secured to a central shaft which is rotatably mounted in a bearing 8 secured to the inner surface of the base of the autoclave tank. The periphery of the rotatably mounted table 4 is also supported by a plurality of rollers 6. One of the rollers 6' is drivable by means of a shaft 2' which passes sealingly through the cylindrical wall of the autoclave tank by means of a mechanical seal or oil seal 3 and which is rotatable in both directions by means of a motor 5 whose direction of rotation can be rapidly and frequently reversed.

As for the first embodiment, in use, a container of liquid to be sterilised is placed on the table 4 and sterilisation is carried out as for the first embodiment. The motor 5 is operated as in the first embodiment, whereby the direction of rotation is frequently stopped and reversed, thereby shaking the table and agitating the liquid to be sterilised.

Alternatively, vibration of the table may be induced without the requirement for a shaft 2, if an ultrasonic transducer is secured to the table, e.g. to the undersurface of the table.

Figure 3:
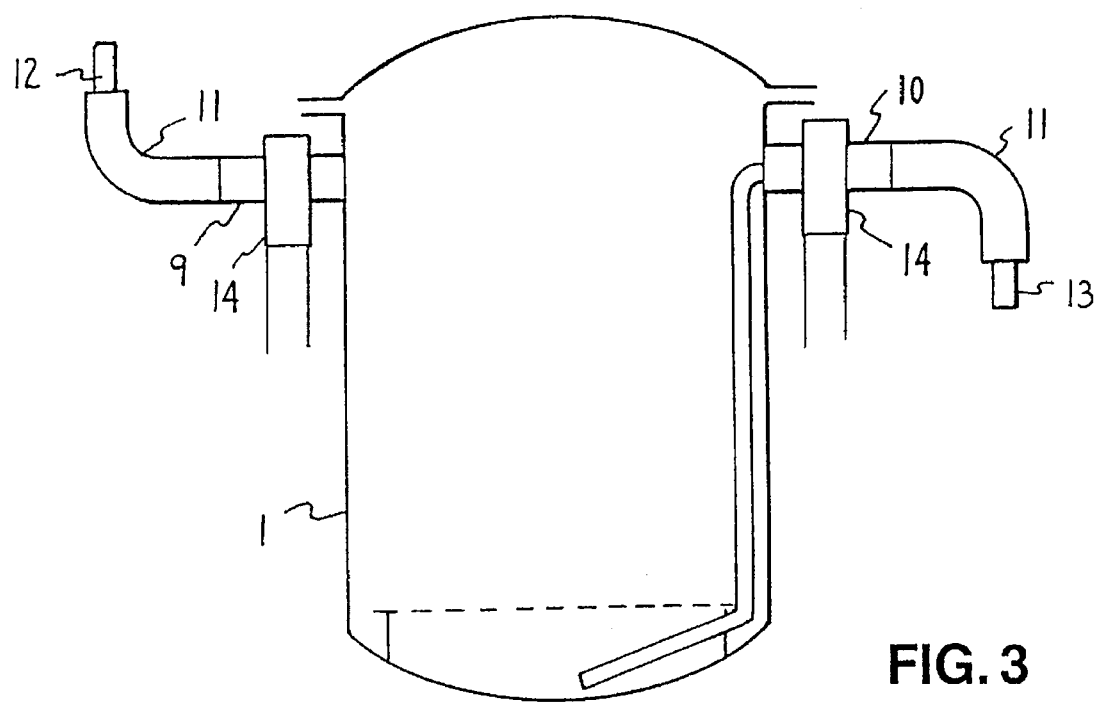

A third embodiment of the present invention, illustrated in FIG. 3, comprises an autoclave tank 1 to which a steam inlet pipe 9 and a steam outlet pipe 10 are connected. The inlet and outlet pipes 9, 10 are each pivotally mounted on bearings 14 and are also pivotally connected to respective elbow joints 11, which are in turn connected to steam supply and discharge pipes 12, 13 respectively.

As for the first two embodiments, a container of liquid to be sterilised is placed on a table 4, which is fixed to the base of the autoclave tank 1. Steam is then generated in the autoclave. The pivotal mounting of the steam inlet 9 and 10 to which the autoclave tank is secured enables the autoclave tank 1 to undergo a pendulum motion about a horizontal axis passing through the longitudinal axis of the inlet and outlet pipes 9, 10. In use, the autoclave tank is shaken in a reciprocating manner, thereby enabling the liquid in the container to be agitated during sterilization and narrowing the temperature distribution within the liquid.

Figure 4:
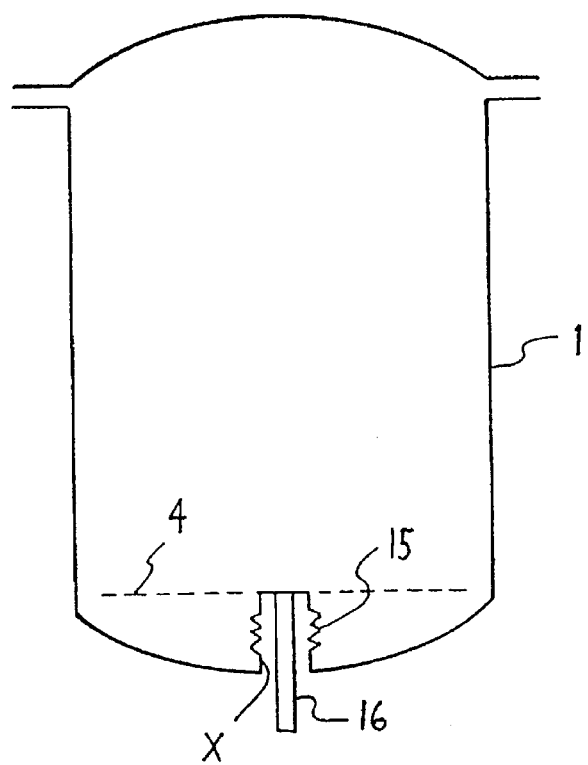

The fourth embodiment of the present invention is illustrated in FIG. 4. The base of the autoclave tank 1 is provided with an aperture X through which a driving rod 16 passes. A shaking or vibrating table 4 is secured to the upper end of the rod, and the aperture through which the rod passes is sealed by means of bellows 15.

In use, a container of liquid to be sterilized is placed on the table 4 within the autoclave tank and steam is generated inside from the autoclave in order to sterilize the liquid. During sterilization, the table 4 is shaken or vibrated by the rod 16. Typically, the rod 16 is reciprocated vertically to agitate the liquid to be sterilized. Alternatively, or in addition, the motion of the rod 16 may be displaced with a seesaw motion, and/or an eccentric rotation in order to maximise the agitation of the liquid and/or to provide a different type of agitation.

Figure 5:
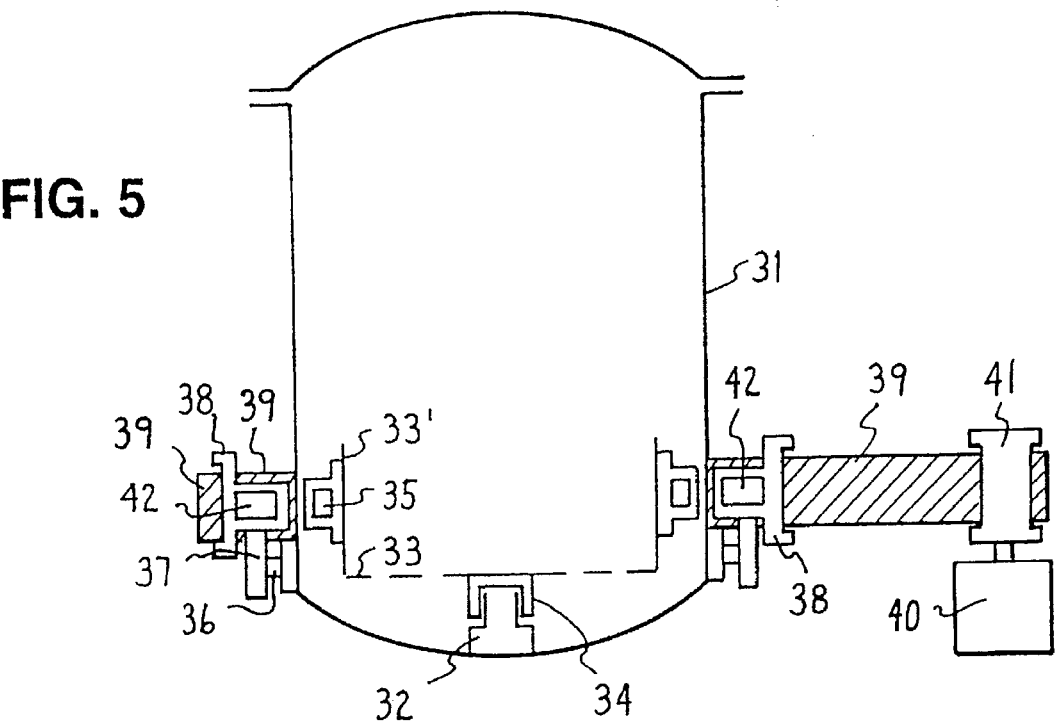

The fifth embodiment of the present invention, illustrated in FIG. 5, comprises a shaking or vibrating table 33, which is rotatably mounted by means of a bearing 34 to a shaft 32 secured to the interior of the base of the autoclave. The shaking table 33 is also provided with an upstanding peripheral rim 33' to the radially outer side of which a plurality of magnets 35 is fixed.

A ring 38 is located around the circumference of the autoclave tank 31 at the same height as the magnets 35 secured to the table 33. The ring 38 carries a plurality of magnets 42 embedded therein, and the number and angular spacing of magnets 42 corresponds with the number and angular spacings of the magnets 35 secured to the table 33. The ring 38 is rotatably mounted on a plurality of rollers 37 secured to shafts 36 which are fixed to the exterior of the autoclave tank 31. The ring 38 is rotatable by means of a belt 39 which passes around a complimentarily-shaped recess in the periphery of the ring and which is drivable by means of an output pulley 41 driven by a motor 40.

The magnets 35 and 42 on the table and ring 38 respectively ensure that the table rotates with the ring 38, but without the requirement for any shaft passing through the wall of the autoclave tank.

As with the previous embodiments, in use, a container of liquid to be sterilized is placed on the table 33 and steam is generated in the autoclave in order to sterilize the liquid.

The motor 40 is operated, preferably in such a way that the direction of rotation is frequently stopped and reversed, as for the first embodiment. The output of the motor is transferred to the ring 38 and to the table 33 by virtue of the magnetic attraction of the magnets 35, 42, thereby agitating the liquid within the autoclave.

In this embodiment, it is not necessary for a rotary shaft to pass through the autoclave tank, so that there is no possibility of leakage of steam from the autoclave. Also, in this embodiment, only a small motor is required, and no thrust load resulting from the magnets is imparted to the bearings.

In the above embodiment, either the magnets 35 on the periphery of the shaking table 33 or the magnets 42 on the rotatable ring 38 may be replaced with a material which is magnetically attracted to a magnet but which is not itself a permanent magnet, if the remaining magnets 42 or 35 are sufficiently strong.

Figure 6:
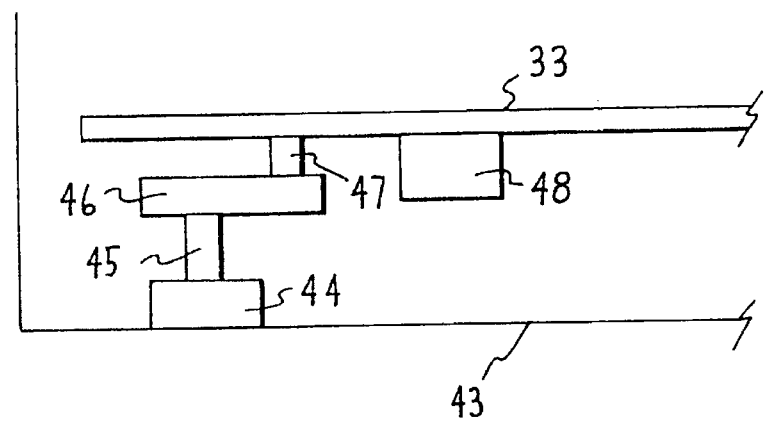
FIGS. 6 and 7 are detailed side elevation cross-sectional of a sixth embodiment of the present invention.
Figure 7:
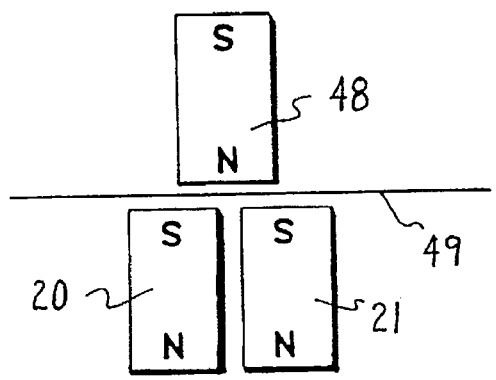

The sixth embodiment, illustrated in FIGS. 6 and 7 is a side elevational cross section of a portion of a large square type of autoclave, and illustrates an eccentric rotary mechanism. The autoclave may be provided with a plurality of mechanisms as shown in FIGS. 6 and 7. Each of the mechanisms comprises a bearing 44 fixed to the base 43 of the autoclave tank and a shaft 45 rotatably mounted in the bearing 44. A horizontally disposed plate 46 is secured to the upper end of the shaft 45 and an output shaft 47 is rotatably and eccentrically mounted on the plate 46, the upper end of the output shaft 47 supporting a shaking or vibrating table 33 and being rotatably secured thereto.

The undersurface of the table 33 is also provided with a permanent magnet 48, as illustrated in FIG. 7. On the external surface of the autoclave tank 31, on the opposite side of a wall 49 of the autoclave tank, a plurality of electromagnets 20, 21 is provided, whose north and south polarities can be changed by application of current in the appropriate direction. In the illustrated arrangement when both of the electromagnets 20, 21 are provided with south poles nearest to the autoclave wall, they attract the north pole of the permanent magnet 48 secured to the undersurface of the shaking table, and conversely when the electromagnets are operated to provide two north poles adjacent to the exterior surface of the autoclave tank, the north pole of the permanent magnet 48 is located adjacent to the north poles of the electromagnets and the magnet 48 is thus repelled therefrom. Thus, it is possible to attract the table towards or repell it away from the electromagnets 20, 21. If the electromagnets are actuated in opposite magnetic directions, the table comes to a position halfway between the two extreme positions mentioned above.

In use, a container of liquid is placed on the table 33 and steam is fed into and out of the autoclave tank via a steam inlet and a steam outlet (not shown) in order to sterilize the liquid. By suitable adjustment of the polarities of the electromagnets, the shaking table can be eccentrically rotated during sterilization without the requirement for a rotary shaft to pass through the wall of the autoclave tank 31. Rapid and frequent reversal of the polarities can provide the required shaking or vibrating, and the eccentric mounting of the table results in a more complex agitation of the liquid.

The seventh embodiment of the present invention, illustrated in FIG. 8, which is a schematic cross-section through part of a large square-type of autoclave, is adapted to produce a combination of eccentric rotation and seesaw motion. The shaking table 33 is provided at its centre with a support post 47, horizontal plate 46, shaft 45 and bearing 44 as in the previous embodiment, but in this embodiment, the support post 47 is secured to the shaking table by means of a flexible joint 22. The four corners of the shaking table are also fixed to the bottom of the tank by means of flexible tubes 23, e.g. silicon rubber tubes.

Sterilization occurs in the same way as for the previous embodiment, with a container of liquid in position on the table 33. During sterilization, the shaking table is eccentrically rotated in the same manner as in the previous embodiment, resulting in a shaking motion consisting of a combination of eccentric motion and, as a result of the flexible joint 22 and the flexible tubes 23, a seesaw motion, i.e. similar to that of a mechanism known as a "belly dancer" mechanism, thereby enabling the liquid to be sterilized to be agitated efficiently by a slow rotation of the shaking table.

The invention is not restricted to the details of the foregoing embodiments. In particular, although in the previous embodiments the table is moved in the horizontal direction, the table can also be driven in the vertical and diagonal directions. Also, although the description states that the direction of rotation of the motor is reversed, it is possible, alternatively or in addition, merely to interrupt the rotation of the motor, i.e. the direction of rotation of the motor need not be reversed.

We claim:

1. An autoclave for agitating and sterilizing a liquid, said autoclave comprising a sterilizer tank having a vertical axis; a table for supporting a liquid, said table having a horizontally disposed upper surface with respect to said vertical axis and said vertical axis extending through said table horizontal upper surface; and means for effecting movement of said table upper surface in a manner such that said liquid is agitated in said sterilizing tank, wherein said movement of said table consists of rotating it in a first direction around said vertical axis, stopping said rotation in said first direction and then rotating said table in the opposite direction around said vertical axis.

2. An autoclave as claimed in claim 1, wherein said movement of said table consists of a cycle of (a) rotating it in a first direction at a speed of from 10 to 100 r.p.m. for a period of from 1 to 20 seconds, (b) stopping for a period of from 1 to 20 seconds, (c) rotating it in the opposite direction at a speed of from 10 to 100 r.p.m. for a period of from 1 to 10 seconds and (4) stopping it again for a period of 1 to 20 seconds and then repeating said cycle.

* * * * *